United States Patent
Hartley et al.

(10) Patent No.: US 9,504,555 B2
(45) Date of Patent: Nov. 29, 2016

(54) ASSEMBLY OF STENT GRAFTS

(75) Inventors: David E. Hartley, Wannanup (AU); Michael Lawrence-Brown, City Beach (AU)

(73) Assignee: Cook Medical Technologies LLC, Bloomington, IN (US)

(*) Notice: Subject to any disclaimer, the term of this patent is extended or adjusted under 35 U.S.C. 154(b) by 2440 days.

(21) Appl. No.: 11/507,115

(22) Filed: Aug. 18, 2006

(65) Prior Publication Data
US 2007/0043425 A1 Feb. 22, 2007

Related U.S. Application Data

(60) Provisional application No. 60/709,411, filed on Aug. 18, 2005.

(51) Int. Cl.
| A61F 2/06 | (2013.01) |
|---|---|
| A61F 2/07 | (2013.01) |
| A61F 2/95 | (2013.01) |
| A61F 2/89 | (2013.01) |

(52) U.S. Cl.
CPC .. *A61F 2/07* (2013.01); *A61F 2/89* (2013.01); *A61F 2002/061* (2013.01); *A61F 2002/065* (2013.01); *A61F 2002/075* (2013.01); *A61F 2002/9505* (2013.01); *A61F 2002/9511* (2013.01); *A61F 2230/005* (2013.01); *A61F 2230/0054* (2013.01); *A61F 2230/0067* (2013.01); *A61F 2250/0039* (2013.01)

(58) Field of Classification Search
CPC ............ A61F 2/07; A61F 2230/0054; A61F 2230/005; A61F 2/89; A61F 2230/0067; A61F 2250/0039; A61F 2002/075; A61F 2002/065; A61F 2002/9511; A61F 2002/9505; A61F 2002/061

USPC ...................... 623/1.12, 1.13, 1.2, 1.23, 1.16
See application file for complete search history.

(56) References Cited

U.S. PATENT DOCUMENTS

| 5,387,235 | A | * | 2/1995 | Chuter | 623/1.11 |
|---|---|---|---|---|---|
| 5,443,500 | A | * | 8/1995 | Sigwart | 623/1.17 |
| 5,456,713 | A | * | 10/1995 | Chuter | 623/1.23 |
| 5,562,726 | A | * | 10/1996 | Chuter | 623/1.35 |
| 5,693,083 | A | * | 12/1997 | Baker et al. | 623/1.11 |
| 5,843,158 | A | * | 12/1998 | Lenker et al. | 623/1.13 |
| 5,843,162 | A | * | 12/1998 | Inoue | 623/1.13 |
| 6,042,605 | A | * | 3/2000 | Martin et al. | 623/1.13 |
| 6,176,875 | B1 | * | 1/2001 | Lenker et al. | 623/1.49 |
| 6,183,504 | B1 | * | 2/2001 | Inoue | 623/1.11 |
| 6,254,629 | B1 | * | 7/2001 | Inoue | 623/1.13 |
| 6,350,277 | B1 | * | 2/2002 | Kocur | 623/1.11 |
| 6,471,722 | B1 | * | 10/2002 | Inoue | 623/1.35 |
| 6,524,335 | B1 | * | 2/2003 | Hartley et al. | 623/1.13 |

(Continued)

FOREIGN PATENT DOCUMENTS

| EP | 1036551 A2 * | 9/2000 |
|---|---|---|
| EP | 1405613 A1 | 4/2004 |

(Continued)

*Primary Examiner* — Richard Louis
(74) *Attorney, Agent, or Firm* — Brinks Gilson & Lione

(57) ABSTRACT

A method of assembling of a stent graft (20) including temporarily diameter reduction arrangements to enable partial release of a stent graft to assist with positioning before complete release. The diameter reduction arrangement includes a release wire (72) and flexible threads (74, 80) extending to struts (76) of a self expanding stent (70) either side of the release wire and being pulled tight. Removal of the release wire enables full expansion of the self expanding stent.

19 Claims, 5 Drawing Sheets

(56) References Cited

U.S. PATENT DOCUMENTS

| | | | |
|---|---|---|---|
| 6,551,350 B1 * | 4/2003 | Thornton et al. | 623/1.13 |
| 6,592,614 B2 * | 7/2003 | Lenker et al. | 623/1.13 |
| 6,741,722 B2 * | 5/2004 | Abe | 382/100 |
| 6,805,706 B2 * | 10/2004 | Solovay et al. | 623/1.15 |
| 6,878,161 B2 * | 4/2005 | Lenker | 623/1.13 |
| 6,916,335 B2 * | 7/2005 | Kanji | 623/1.11 |
| 6,929,659 B2 * | 8/2005 | Pinchuk | 623/1.13 |
| 6,974,471 B2 * | 12/2005 | Van Schie et al. | 623/1.12 |
| 7,022,132 B2 * | 4/2006 | Kocur | 623/1.11 |
| 8,118,855 B2 * | 2/2012 | Hartley | A61F 2/07 623/1.12 |
| 8,377,113 B2 * | 2/2013 | Hartley | A61F 2/07 623/1.23 |
| 2002/0165603 A1 * | 11/2002 | Thornton et al. | 623/1.13 |
| 2002/0177890 A1 * | 11/2002 | Lenker | 623/1.12 |
| 2003/0088305 A1 * | 5/2003 | Van Schie et al. | 623/1.12 |
| 2003/0149475 A1 * | 8/2003 | Hyodoh et al. | 623/1.19 |
| 2004/0098084 A1 * | 5/2004 | Hartley et al. | 623/1.11 |
| 2007/0142896 A1 | 6/2007 | Anderson et al. | |

FOREIGN PATENT DOCUMENTS

| | | |
|---|---|---|
| WO | 98/53761 A1 | 12/1998 |
| WO | 99/29262 A1 | 6/1999 |
| WO | WO 03034948 A1 * | 5/2003 |
| WO | 2004/019823 A1 | 3/2004 |
| WO | 2006/007389 A1 | 1/2006 |
| WO | PCT/US2006/032683 | 1/2007 |

* cited by examiner

ASSEMBLY OF STENT GRAFTS

CROSS-REFERENCE TO RELATED APPLICATIONS

This application claims priority of provisional application Ser. No. 60/709,411, filed Aug. 18, 2005.

TECHNICAL FIELD

This invention relates to a medical device and more particularly to a stent graft for mounting onto a deployment device for endovascular introduction.

BACKGROUND OF THE INVENTION

This invention will be particularly discussed in relation to stent grafts for placement into the thoracoabdominal aorta for the treatment of aneurysms and more specifically in relation to juxtarenal placement. The invention, however, is not so restricted and may be applied to stent grafts for placement in any lumen of the human or animal body.

The segment of aorta between the celiac and renal arteries is the best endowed with adventitial elastin, the most stable, and the last to dilate. Aneurysms of this area are associated with aneurysms of less stable areas in the descending thoracic aorta, infrarenal aorta, or both. Surgical repair of the thoracoabdominal aorta often involves wide exposure through long, multi-cavity incisions, followed by periods of visceral ischemia. Despite advances in surgical technique and perioperative care, the mortality and morbidity rates remain high, especially in patients who are old, sick, or have already undergone open surgical repair of an adjacent segment of the aorta. In such cases, an endovascular alternative would be welcome, yet endovascular methods of thoracoabdominal and pararenal aortic repair have been slow to develop. The challenge has been to exclude the aortic aneurysm while maintaining flow to its visceral branches.

It is roughly 4 years since two distinctly different approaches to this problem were reported. The two devices were: a bifurcated abdominal aortic stent-graft with fenestrations for the renal and superior mesenteric arteries, and a thoracoabdominal stent-graft with branches for the celiac, superior mesenteric and renal arteries. In recent years, the distinctions between fenestrated and multi-branched stent-grafts have been blurred by the emergence of many hybrid devices with features such as Nitinol ringed fenestrations, externally cuffed fenestrations, internally cuffed fenestrations, external spiral cuffs and axially-oriented cuffs or branches, both external and internal. Each element has advantages and disadvantages, and each combination has a different role, as described below.

There now exists a family of devices, which share several key features. In each of them, a barbed uncovered Z-stent anchors the proximal end, and a single proximal orifice attaches to a non-dilated segment of aorta (or previously inserted prosthesis). They all distribute blood through multiple branches, cuffs or holes (fenestrations), and they have series of Z-stents and Nitinol rings, providing support from one end of the stent-graft to the other.

In cases of juxtarenal AAA, the rim of non-dilated infrarenal aorta is too short for secure hemostatic implantation of an unfenestrated stent-graft. There is only enough room in the neck for the proximal end of the proximal stent; the rest of this covered stent expands into the aneurysm, assuming a conical shape. Under these circumstances, there is insufficient apposition between the stent-graft and the aorta to achieve a reliable seal. Properly positioned fenestrations (holes) provide a route for flow through the stent-graft into the renal arteries, thereby allowing the proximal end of the stent-graft to be placed higher in the non-dilated pararenal aorta where it assumes a cylindrical shape. The dual goals of renal perfusion and aneurysm exclusion are achieved only when the fenestration is positioned precisely over the renal orifices, and the outer surface of the stent-graft around the fenestration is brought into close apposition with the inner surface of the aorta around the renal orifice. Typical fenestrated technique uses a bridging catheter, sheath or balloon to guide each fenestration to the corresponding renal orifice, and a bridging stent to hold it there. Stent-graft deployment has five main stages: extrusion of the half-open stent-graft, trans-graft renal artery catheterization, complete stent-graft expansion, renal stenting, and completion of the aortic exclusion with bifurcated extension into the iliac arteries.

The three forms of fenestration in common use are the large fenestration, the scallop and the small fenestration. A large fenestration is used only when the target artery is well away from the aneurysm. No bridging stent is required, or even feasible, since one or more stent struts cross the orifice of a large fenestration. A scallop is essentially a large open-topped fenestration. In many cases, the presence of a scallop for the superior mesenteric artery allows sufficient separation (>15 mm) between proximal margin of the stent-graft and the middle of the renal orifices. Small fenestrations are commonly placed over both renal arteries, and held there by bridging stents. Stent struts cannot cross the orifice of a small fenestration. Small fenestrations are therefore confined to the lower halves of the triangular spaces between adjacent stent-struts.

Localized juxtarenal aneurysms or pseudoaneurysms require no more than a single cylindrical fenestrated stent-graft, but most cases of infrarenal aneurysm extend to the aortic bifurcation and require bilateral iliac outflow through a bifurcated stent-graft. The combination of a fenestrated proximal component with a bifurcated distal component is called a composite stent graft. Dividing the stent-graft into two components separates the two halves of the procedure. The operator need not be concerned about the position or orientation of the bifurcation while inserting the fenestrated proximal component, or about the position and location of the fenestrations while inserting the bifurcated distal component. The composite arrangement also separates the fenestrated proximal component from the large caudally directed hemodynamic forces that act mainly upon the bifurcation of the distal component. A small amount of slippage between the two is preferable to any proximal component migration, where even a few millimeters of movement would occlude both renal arteries. Indeed, the low rate of renal artery loss is testimony to the accuracy of stent-graft deployment and the stability of stent-graft attachment.

The positioning of the fenestration is therefore very important to avoid renal occlusion.

Positioning is further complicated because the diameter of a stent graft is deliberately made larger than the diameter into which it is to be placed to allow for accurate sealing against the vessel wall, possible errors in sizing and subsequent relaxation of the vessel wall. Hence, once released a stent graft with self expanding stents will take up apposition against the vessel wall and it will be difficult if not impossible to reposition it.

It is to the ability to position after initial release of a stent graft from a deployment device that the present invention is directed or at least to provide a practitioner with a useful alternative.

Throughout this specification the term distal with respect to a portion of the aorta, a deployment device or a prosthesis is the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form therefor the invention is said to reside in a method of reducing the diameter of the stent graft during deployment comprising the step applying temporary diameter reducing ties to at least a portion of the stent graft.

In a further form the invention comprises a temporary diameter reduction constraint arrangement for a stent graft, the stent graft comprising a biocompatible graft material tube of a selected diameter and a plurality of self expanding stents fastened thereto, the constraint arrangement comprising at least one release wire extending longitudinally along the graft material tube and stitched thereinto and at least one circumferential thread engaged around the release wire and a portion of the stent graft circumferentially spaced a selected distance away from the release wire and drawn tight and tied to reduce the circumference and hence the overall diameter of the stent graft.

Preferably the circumferential thread extends circumferentially in each direction from the release wire.

The stents are preferably zig-zag stents comprising struts and bends therebetween and the engagement of the flexible thread into the graft material includes the engagement of the thread around a strut of the self expanding stent. Preferably the engagement of the threads with the respective struts is intermediate the ends of the struts.

The selected distance can for instance be reduced by from 50 to 75%.

There can be two release wires and a circumferential thread extending circumferentially in each direction from each of the release wires at a plurality of positions along the release wires to hold the stent graft at a reduced diameter of the stent graft along the length of the stent graft. Preferably the positions along the length of the release wires corresponds with a middle portion of the struts of the self expanding stents along the length of the stent graft.

In a further form the invention comprises a method of temporarily reducing the diameter of at least a portion of a self expanding stent graft, the stent graft comprising a tubular body of a biocompatible graft material and a plurality of self expanding stents, the method comprising the steps of;

a) stitching a release wire longitudinally along the stent graft;

b) looping a first flexible thread around the release wire and extending the first flexible thread laterally around the circumference of the stent graft to a position a selected distance from the release wire;

c) engaging the first flexible thread into the graft material, and d) drawing the ends of the thread together and tying ends of the thread, whereby the selected distance is reduced thereby temporarily reducing the overall diameter of the stent graft.

The method can further comprise the steps of;

e) passing a second flexible thread around the release wire and extending the second flexible thread laterally around the circumference of the stent graft in the opposite direction to the first flexible thread to a position a selected distance from the release wire;

f) engaging the second flexible thread into the graft material, and g) drawing the ends of the second thread together and tying ends of the thread, whereby the selected distance is reduced thereby reducing the overall diameter of the stent graft.

The method can further comprise the alternative steps of;

e) passing a second flexible thread around the first flexible thread and extending the second flexible thread laterally around the circumference of the stent graft in the opposite direction to the first flexible thread to a position a selected distance from the release wire;

h) engaging the second flexible thread into the graft material, and i) drawing the ends of the second thread together and tying ends of the thread, whereby the selected distance is reduced thereby temporarily reducing the overall diameter of the stent graft.

The method can further comprise the steps of;

j) stitching a second release wire longitudinally along the stent graft parallel to and spaced apart from the first release wire;

k) looping a third flexible thread around the second release wire and extending the third flexible thread laterally around the circumference of the stent graft to a position a selected distance from the second release wire;

l) engaging the third flexible thread into the graft material, and m) drawing the ends of the thread together and tying ends of the thread, n) passing a fourth flexible thread around the around the third flexible thread and extending the fourth flexible thread laterally around the circumference of the stent graft in the opposite direction to the third flexible thread to a position a selected distance from the second release wire;

o) engaging the fourth flexible thread into the graft material, and p) drawing the ends of the fourth thread together and tying ends of the thread, whereby the selected distance is reduced thereby temporarily reducing the overall diameter of the stent graft.

The method can further comprise applying a plurality of flexible threads in each circumferential direction from each release wire at a plurality of positions along the release wires to temporarily reduce the diameter of the stent graft along the length of the stent graft. Preferably the engagement of the threads with the respective struts of the stent grafts is intermediate the ends of the struts.

BRIEF DESCRIPTION OF THE DRAWING

This then generally describes the invention but to assist with understanding reference will now be made to the accompanying drawings which show preferred embodiments of the invention.

In the drawings.

DETAILED DESCRIPTION

Figure 1:
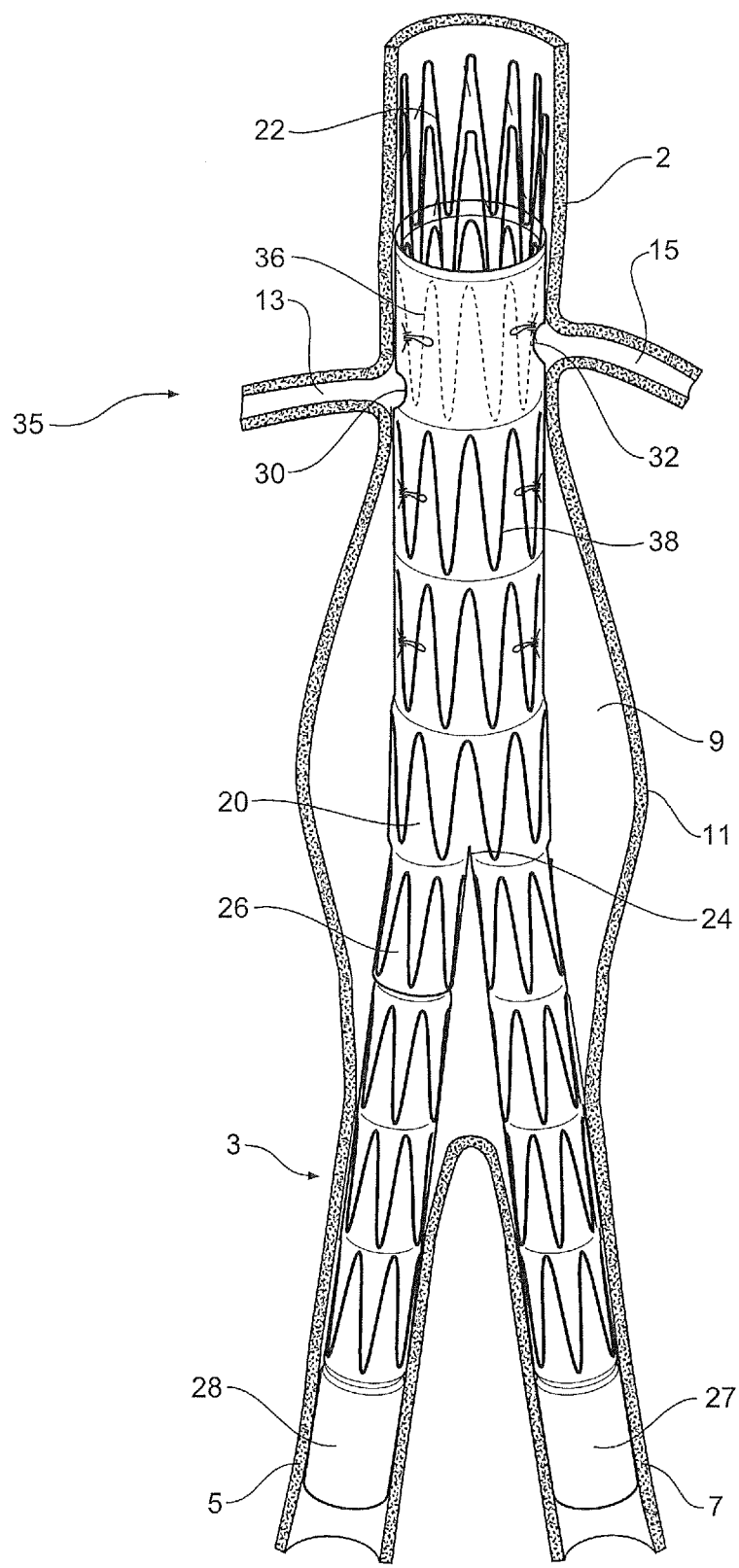
FIG. 1 shows a schematic view of an aneurysed aorta with a bifurcated and fenestrated stent graft deployed into it.

Now looking more closely at the drawings and in particular FIG. 1 it can be seen that there is schematically shown an aorta 2 extending down to an aortic bifurcation at 3 and into two iliac arteries 5 and 7. An aneurysm 9 defined by a bulge in the aorta wall 11 extends from near to the aortic bifurcation 3 nearly to the renal arteries 13 and 15. There is insufficient non-aneurysed length of the aorta distally of the renal arteries and hence to place a stent graft to bypass the aneurysm it is necessary to place some of the stent graft proximally of the renal arteries.

This embodiment of the invention is discussed in relation to a bifurcated stent graft having a longer leg for extending into one iliac artery and a shorter leg into which a leg extension may be deployed for the contralateral iliac artery but the invention is not so limited and may also be used for a composite stent graft in which the fenestrations are in a proximal tubular portion of the composite stent graft and if necessary a further bifurcated portion of stent graft is used to extend down to the iliac arteries.

The stent graft 20 has a bifurcation 24 and a long leg 27 extending down iliac artery 7 and a short leg 26 directed towards iliac artery 5. A leg extension 28 is connected into the short leg 26 and extends down the iliac artery 5. The stent graft 20 has a proximal internal stent 36 and a plurality of external stents 38 along the length of its tubular body. At the renal arteries 13 and 15 there are fenestrations 30 and 32 respectively for allowing access to the renal arteries and it is to the placement of these renal fenestrations on the stent graft so that they match up with the renal arteries when the stent graft is deployed into the aorta that the present invention is directed. Methods of deployment of such a stent graft are described in PCT Patent Publication Number WO98/53761 entitled "A Prosthesis and a Method of Deploying a Prosthesis". These features and other features disclosed in PCT Patent Publication Number No. WO98/53761 could be used with the present invention and the disclosure of PCT Patent Publication Number No. WO98/53761 is herewith incorporated in its entirety into this specification.

Although the renal arteries in FIG. 1 are depicted as extending laterally either side of the aorta, in fact the position of the renal arteries is very variable and are sometimes closer together towards the anterior surface of the aorta and can be positioned more or less apart longitudinally.

Figure 2A:
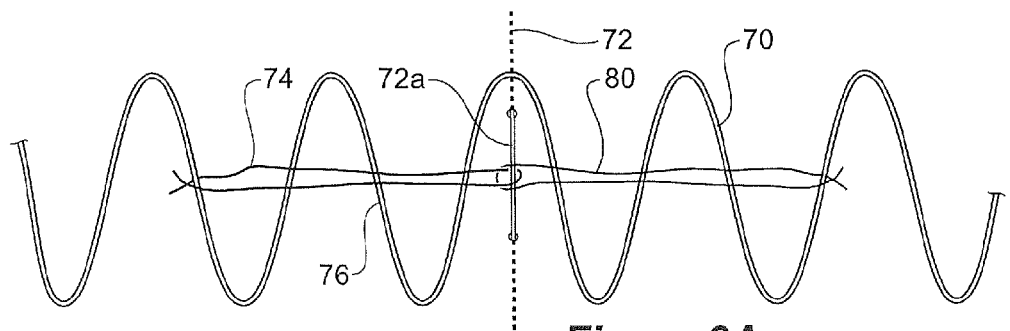
FIGS. 2A and 2B show schematically how one arrangement of a diameter reducing ties are applied to a stent graft.
Figure 2B:
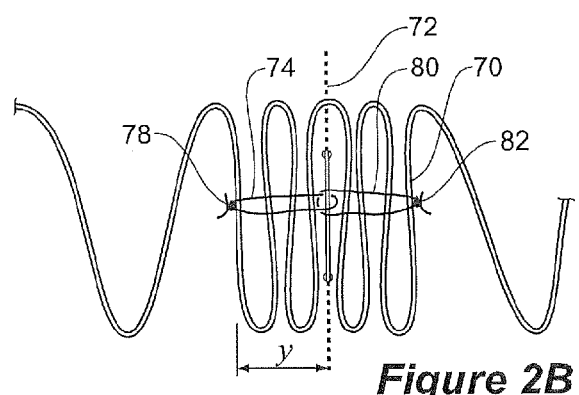

FIGS. 2A and 2B show schematically one embodiment of diameter reducing tie according to the present invention. In this drawing the graft material of a stent graft is not shown and only a portion of a self expanding stent is shown stretched out flat.

As can be seen in FIG. 2A, a self expanding stent 70 which would extend around the tubular body of a stent graft and be stitched to the stent graft is shown. A release wire 72 is stitched longitudinally along the stent graft as can be seen in more detail in FIG. 4A with a stitch 72a of the release wire being exposed to the outside of the stent graft in the region of the self expanding stent 70.

A first suture thread 74 of a flexible material is passed around the release wire 72 and extended out to one side of the release wire over the struts 76 of the stent graft to pass over three struts and to be looped around a fourth strut and into the graft material. The suture thread 74 is then pulled tight and knotted as shown in FIG. 2B with a knot 78 so that the struts between the release wire 72 and the knot 78 are pulled closer together against the resilient force of the self expanding stent.

A similar action is carried out to the other side of the release wire with a second suture thread 80 of a flexible material. In this case the thread 80 can either pass around the release wire 72 or is passed underneath the two strands of the thread 74 and over the release wire 72 and then it can be passed over three struts and then looped around a fourth strut and into the graft material and pulled tight and knotted at 82.

Figure 3A:
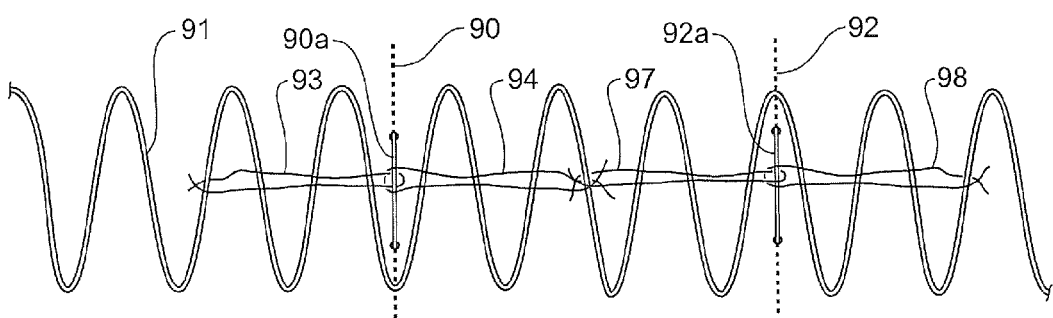
FIGS. 3A and 3B show an alternative embodiment of diameter reducing ties intended for use with a stent graft.
Figure 3B:
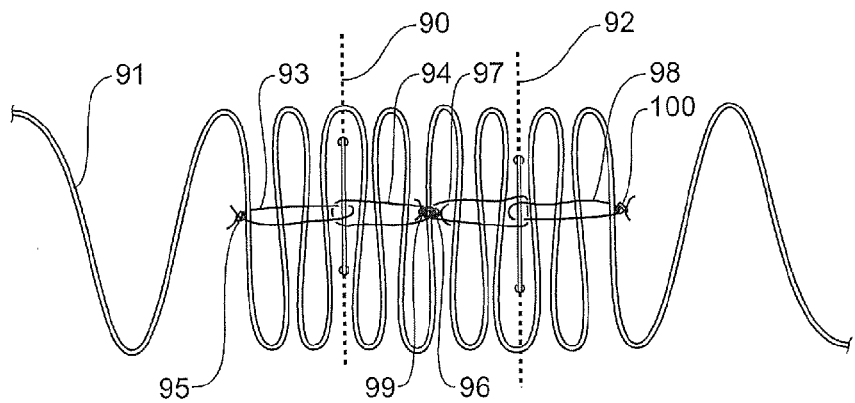

The reduction in distance between the release wire 72 and the knot 78 may be from 50 to 75 percent. For instance if the distance x in FIG. 2A is 15 millimeters around the circumference of the stent graft from the release wire 72 to the strut at which the knot 78 is placed then this can be reduced to 5 millimeters as shown by the dimension y in FIG. 2B. With two diameter reducing ties, one to each side of the release wire 72, therefore a total circumference reduction of 20 millimeters can be achieved which will change the diameter of a 36 millimeter stent graft to approximately 28 millimeters. This can be less than the diameter of the aorta in that region which means that the stent graft will still be manoeuvrable within the aorta while still mounted onto the deployment device but partially freed by the withdrawal of a containing sheath.

Where a greater amount of diameter reduction is desirable double diameter reducing ties may be used as depicted in FIGS. 3A and 3B.

In this embodiment two release wires 90 and 92 are used parallel to each other and spaced apart by 6 or 7 struts of a self expanding stent 91. The two release wires 90 and 92 are stitched longitudinally along the stent graft as can be seen in more detail in FIG. 4A with stitches 90a and 92a being exposed to the outside of the stent graft in the region of the self expanding stent 91. A first suture 93 extends from one side of the release wire 90 and a second suture 94 extends to the other side of the release wire 90 and they are knotted off at 95 and 96. Similarly sutures 97 and 98 are extended either side of the release wire 92 and are knotted off at 99 and 100. Generally the knots 96 and 99 go on either side of the same strut.

By using these double diameter reducing ties for instance a reduction in circumference of up to 40 millimeters may be obtained for a 36 millimeter diameter stent graft which will give a final diameter of approximately 24 millimeters. Once again with this reduction in diameter movement of the stent graft for final positioning can be easily achieved.

Figure 4A:
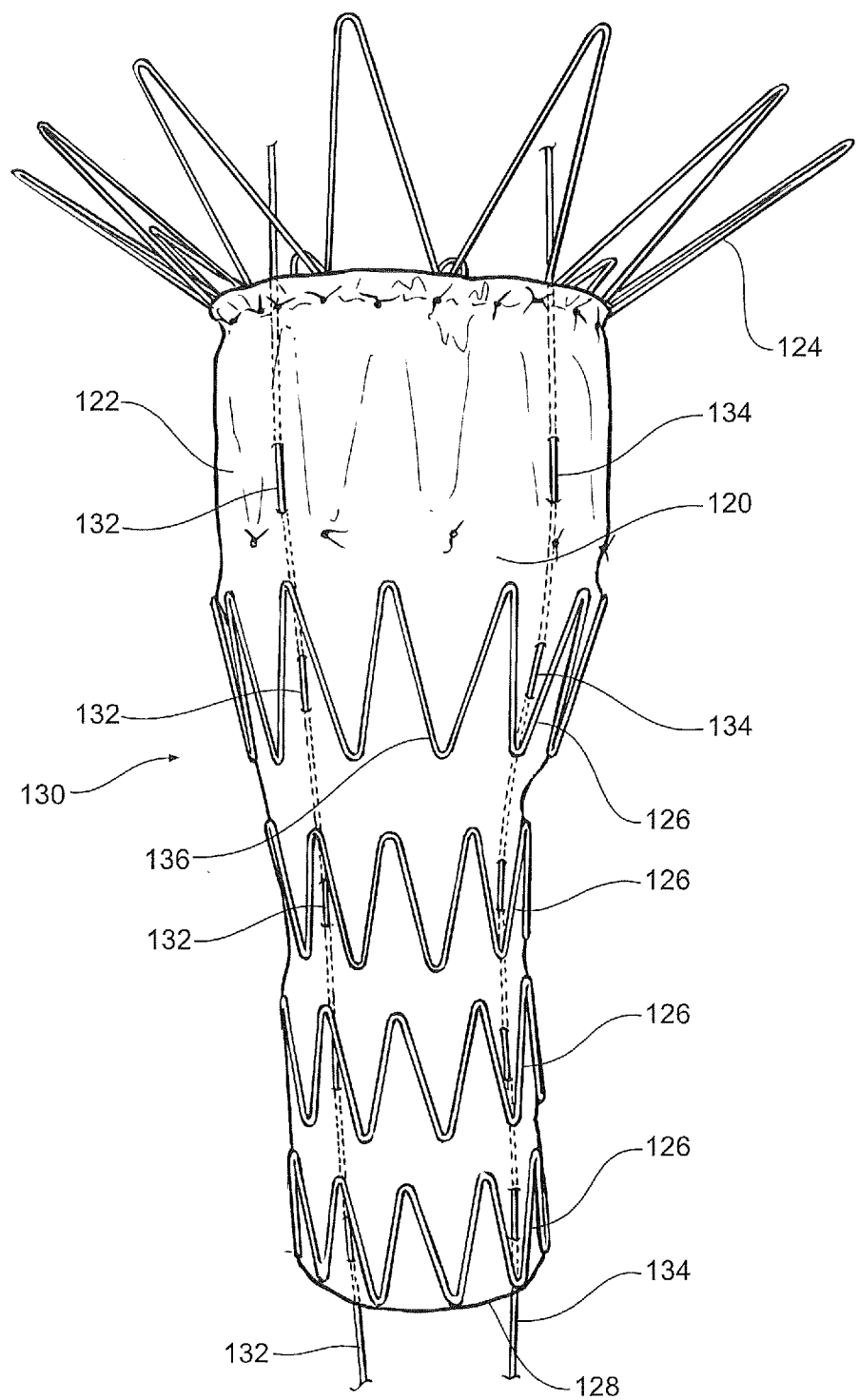
FIGS. 4A, 4B and 4C show a stent graft in various stages of application and release of double diameter reducing ties on a stent graft.
Figure 4B:
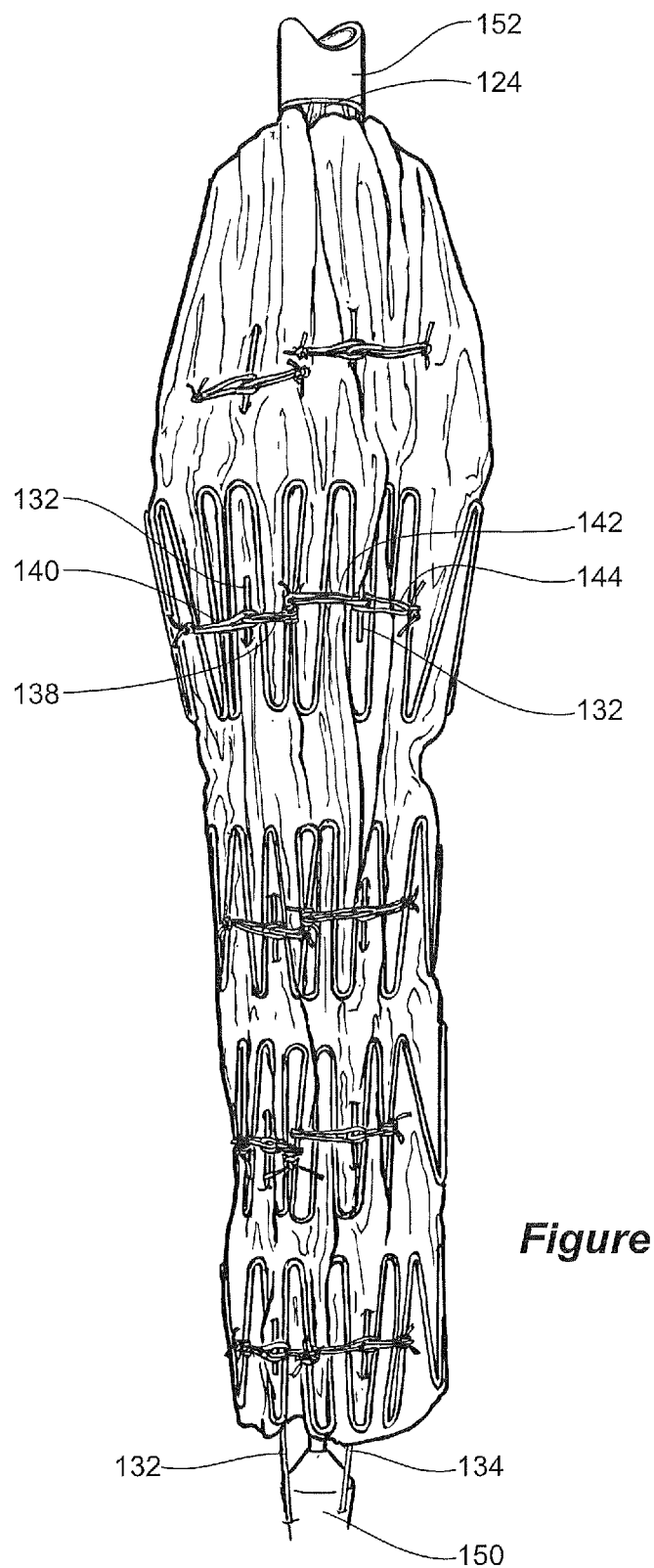
Figure 4C:
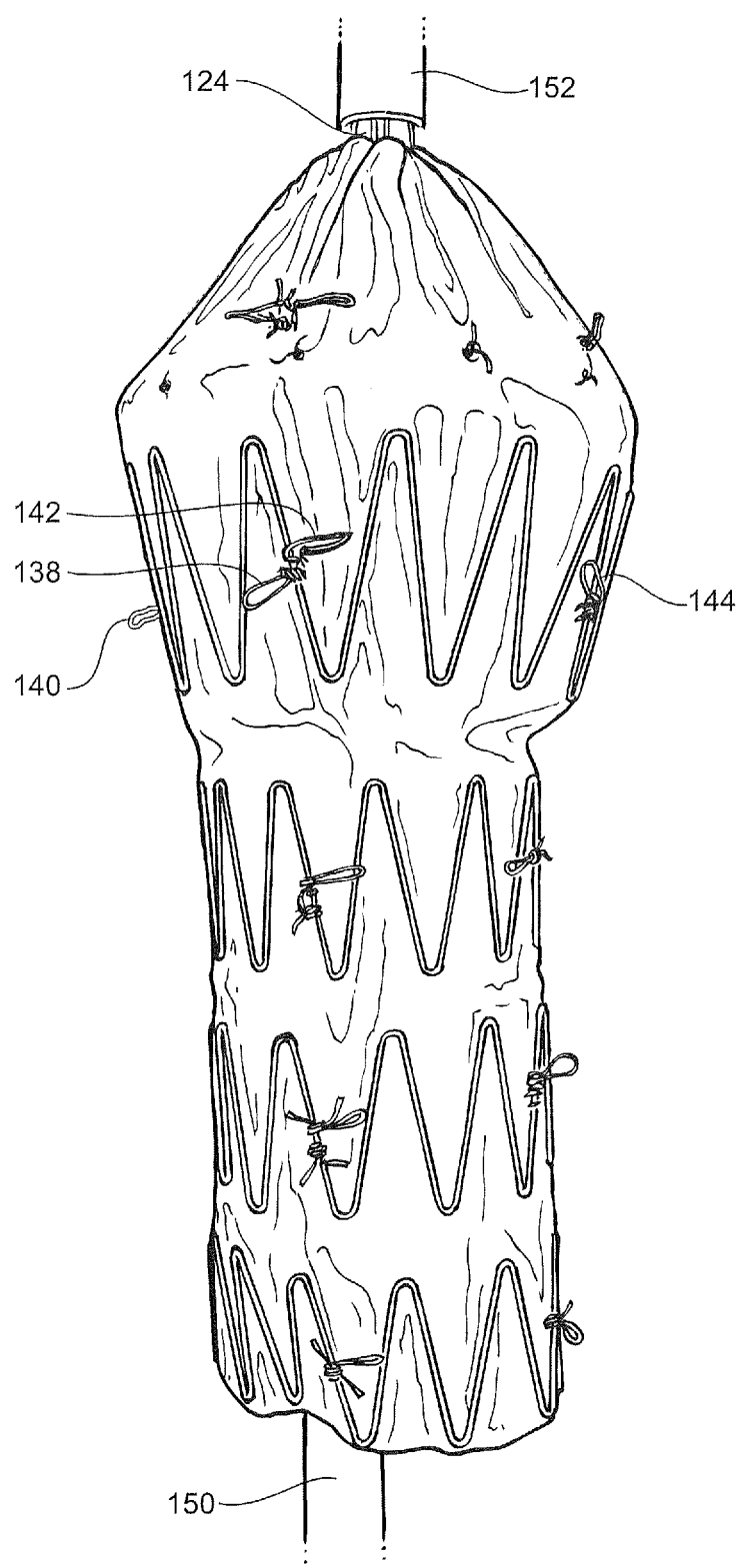

FIGS. 4A, 4B and 4C show a stent graft with various stages of fitting and release of diameter reducing ties.

FIG. 4A shows a more proximal portion of a composite stent graft for mounting into the aorta. The stent graft includes a tubular body 120 with an internal zigzag self expanding stent 122 at its proximal end and an exposed proximally extending stent 124 mounted to the proximal end of the tubular body 120. Further external self expanding stents 126 are supplied along the length of the body towards the distal end 128. It will be noted the tubular body 120 tapers at 130 so that it is a first selected diameter at the proximal end and a slightly smaller diameter further down the length of the tubular body.

This embodiment of the invention will be discussed particularly in relation to installation of double diameter reducing ties.

The first stage is the placement of release wires 132 and 134 which extend longitudinally along the tubular body and are stitched in and out of the tubular body. Stitches can be seen on the exterior of the tubular body in regions coinciding with the intermediate region of the struts of each of the exposed stents. In the region designated as 130 for instance a suture is placed around the release wire and extended across about three struts of the zigzag stent 126 to strut 136 where it is passed around the strut 136 and into the graft material of the tubular body 120 and pulled tight as shown at 138 in FIG. 4B. Similarly a suture 140 extended from the other direction from the release wire 132 for about three struts passed around a strut and into the graft material of the tubular body 120 and then pulled tight.

A similar extension of sutures in each direction from release wire 134 are installed to compress the other side. The suture 142 which extends back towards the release wire 132 is joined to the same strut 136 as the suture 138. The suture 144 extends in the opposite direction from the release wire 134.

This process is repeated with the other exposed stents 126 and the internal stent 122. In the case of the internal stent 122 the sutures are inserted through the material of the tubular body 120 to go around the stents where they are knotted but otherwise remain outside of the tubular body. This gives the result as shown in FIG. 4B where the diameter of the stent graft is considerably reduced. Diameter reducing ties may be either placed along the entire length of the stent graft so that the stent graft remains manoeuvrable after its partial release as discussed above or can be confined to only the parts of the stent graft that are larger in diameter than the vessel lumen into which it is to be placed.

FIG. 4B shows the stent graft mounted onto a deployment device with a pusher catheter 150 at one end and a nose cone capsule 152 into which the proximally extending stent 124 is received at the other end. At this stage a containing sheath has been withdrawn onto the pusher catheter so that the stent graft has partially expanded under the influence of self expanding stents but complete expansion has been prevented by the diameter reducing ties 138, 140, 142 and 144.

FIG. 4C shows the stent graft still mounted onto the deployment device so that the exposed stent 124 is still received in the capsule 152 but the release wires 132 and 134 have been withdrawn so that the diameter reducing ties are released. It will be noted that the sutures 140, 138, 142, and 144 remain on the outside of the stent graft. This is not a problem as they do not interfere with blood flow and may assist with adhesion of the stent graft onto the wall of the aorta.

In an alternative arrangement where space permits two sets of double diameter reducing ties may be used with one set of double diameter reducing ties and trigger wire placed anterior to the renal arteries and another set of double diameter reducing ties and trigger wire placed posterior to the renal arteries.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A temporary diameter reduction constraint arrangement for a stent graft in combination with a stent graft,
    the stent graft comprising a tube of biocompatible graft material forming a tubular body having a diameter and a plurality of self expanding stents fastened thereto along the length of the tube of biocompatable graft material, the plurality of stents including a first stent at one end of the tube, a second stent at the other end of the tube, and at least one intermediate stent between the first and second stents,
    the constraint arrangement comprising at least one release wire extending longitudinally along the graft material tube,
    the at least one release wire being stitched into and along the length of the tubular body with at least one stitch of the release wire being exposed to the outside of the tubular body in the region of the intermediate stent,
    the constraint arrangement further comprising at least one loop of thread extending at least partially circumferentially about the tubular body and with one end of the at least one loop engaged around the at least one stitch of the release wire and another end of the loop engaged around a portion of the stent graft circumferentially spaced a selected distance away from the release wire to at least partially gather the material of the graft and reduce the overall diameter of the stent graft.

2. The constraint and stent graft arrangement of claim 1, wherein the at least one stitch comprises a plurality of externally exposed stitches and the plurality of self expanding stents each comprises a strut having an intermediate region, wherein at least one stitch of the plurality of externally exposed stitches coinciding with an intermediate regions of at least one strut of each of the plurality of self expanding stents.

3. The constraint and stent graft arrangement of claim 1, wherein the stents are zig-zag stents comprise struts with bends therebetween, and the end of the loop circumferentially spaced from the release wire is engaged about a strut of the intermediate stent.

4. The constraint and stent graft arrangement of claim 1, wherein the selected distance is reduced from 50% to 70%.

5. The constraint and stent graft arrangement of claim 1, comprising two release wires wherein each release wire has a first loop of thread extending circumferentially away from the release wire in one direction and a second loop of thread extending circumferentially away from the release wire in an opposite direction at a plurality of positions along the release wires to hold the stent graft at a reduced diameter of the stent graft along the length of the stent graft.

6. A method of temporarily reducing the diameter of at least a portion of a self expanding, the stent graft comprising a tubular body of a biocompatible graft material and a plurality of self expanding stents attached to the tubular body along the length of the tubular body, the plurality of stents including a first end stent, a second end stent and an intermediate stent between the first and second end stents, the method comprising the steps of;
    a) extending a release wire longitudinally along the tubular body and stitching the release wire into the tubular body wherein at least one stitch of the release wire is exposed to the outside of the tubular body in the region of the intermediate stent and engages a first flexible thread;
    b) looping a first end of the first flexible thread around the exposed stitch of the release wire and extending the first flexible thread laterally around the circumference of the stent graft such that a second end of the first flexible thread is positioned a selected distance from the release wire;

c) engaging the second end of the first flexible thread to the stent graft at the selected distance from the release wire; and
d) drawing the ends of the first flexible thread together and tying the ends of the first flexible thread to reduce to temporarily reduce the selected distance and the overall diameter of the stent graft.

7. The method of claim 6, wherein the stents are zig-zag stents comprising struts with bends therebetween and the step of engaging the second end of the flexible thread to the stent graft includes engaging the first flexible thread around a strut of the intermediate stent.

8. The method of claim 6, further comprising the steps of;
e) passing a first end of a second flexible thread around the stitch of the release wire and extending the second flexible thread laterally around the circumference of the stent graft in the opposite direction to the first flexible thread such that a second end of the second flexible thread is positioned a selected distance from the release wire;
f) engaging the second end of the second flexible thread to the stent graft at the selected distance from the release wire; and
g) drawing the ends of the second flexible thread together and tying the ends of the second flexible thread, to reduce to temporarily reduce the selected distance and the overall diameter of the stent graft.

9. The method of claim 6, wherein the selected distance is reduced by from 50 to 75%.

10. The method of claim 6, further comprising the steps of;
e) engaging a first end of a second flexible thread with the second end of the first flexible thread and extending the second flexible thread laterally around the circumference of the stent graft in the opposite direction to the first flexible thread to a position a selected distance from the release wire;
f) engaging the second end of the second flexible thread to the stent graft at the selected distance from the release wire; and
g) drawing the ends of the second flexible thread together and tying the ends of the second flexible thread, to reduce to temporarily reduce the selected distance and the overall diameter of the stent graft.

11. The method of claim 8, further comprising the steps of;
h) extending a second release wire longitudinally along the stent graft parallel to and spaced apart from the first release wire and stitching the second release wire into the tubular body wherein a stitch of the second release wire is exposed to the outside of the tubular body in another region of the self expanding stent circumferentially spaced from the first region;
i) looping a first end of a third flexible thread around the stitch of the second release wire and extending the third flexible thread laterally around the circumference of the stent graft such that a second end of the third flexible thread is positioned a selected distance from the second release wire;
j) engaging the second end of the third flexible thread to the stent graft at the selected distance from the release wire; and
k) drawing the ends of the third flexible thread together and tying the ends of the third flexible thread;
l) engaging a first end of a fourth flexible thread with the second end of the third flexible thread and extending a second end of the fourth flexible thread laterally around the circumference of the stent graft in the opposite direction to the second end of the third flexible thread to a position a selected distance from the second release wire; the fourth flexible thread comprising ends;
m) engaging the second end of the fourth flexible thread with the stent graft; and
n) drawing the ends of the fourth flexible thread together and tying the ends of the fourth flexible thread, to reduce to temporarily reduce the selected distance and the overall diameter of the stent graft.

12. The method of claim 6, comprising applying a plurality of flexible threads in addition to the first flexible thread to reduce the diameters along the length of the stent graft, by repeating the steps of looping, engaging, and drawing, with a first and second end of each of the flexible threads of the plurality of flexible threads.

13. A method of temporarily reducing the diameter of at least a portion of a self expanding stent graft, the stent graft comprising a tubular body of a biocompatible graft material and a plurality of self expanding stents along the length of the tubular body, wherein the plurality stents are zig-zag stents comprising struts with bends therebetween, and wherein the plurality of stents includes a first end stent, a second end stent and an intermediate stent between the first and second end stents,
the method comprising the steps of;
a) extending a release wire longitudinally along the stent graft and stitching the release wire into the tubular body such that at least one a stitch of the release wire is exposed to the outside of the tubular body in the region of the intermediate stent;
b) looping a first end of a first flexible thread around the release wire and extending the first flexible thread laterally around the circumference of the stent graft to a first selected strut of the intermediate stent a selected distance from the release wire;
c) engaging a second end of the first flexible thread around the selected strut; and
d) drawing the ends of the first flexible thread together and tying the ends of the thread to each other to reduce the selected distance and the overall diameter of the stent graft.

14. The method of claim 13 further comprising the steps of;
e) looping a first end of a second flexible thread around the release wire or engaging the first end of the second flexible thread with the second end of the first flexible thread and extending the second flexible thread laterally around the circumference of the stent graft in the opposite direction to the first flexible thread to a second selected strut of the intermediate stent a selected distance from the release wire;
f) engaging a second end of the second flexible thread around the second selected strut; and
g) drawing the ends of the second flexible thread together and tying the ends of the thread to reduce the selected distance and the overall diameter of the stent graft.

15. The method of claim 13, wherein the selected distance is reduced by from 50 to 75%.

16. The method of claim 13, comprising applying a plurality of flexible threads to reduce the diameters along the length of the stent graft.

17. The method of claim 13, further comprising the steps of;
e) extending a second release wire longitudinally along the stent graft parallel to and circumferentially spaced apart from the first release wire and stitching the second release wire into the tubular body wherein a stitch of the second release wire is exposed to the outside of the tubular body in the region of the intermediate stent;

f) looping a first end of a third flexible thread around the second release wire and extending the third flexible thread laterally around the circumference of the stent graft to a position a selected distance from the second release wire;

g) engaging a second end of the third flexible thread around a second selected strut of the self-expanding stent;

h) drawing the ends of the third flexible thread together and tying the ends of the thread;

i) engaging a first end of a fourth flexible thread with the third flexible thread and extending the fourth flexible thread laterally around the circumference of the stent graft in the opposite direction to the third flexible thread to a position a selected distance from the second release wire;

j) engaging the fourth flexible thread around a third selected strut of the intermediate stent;

k) drawing the ends of the fourth flexible thread together and tying the ends of the thread to reduce the overall diameter of the stent graft.

18. The method of claim 17 comprising applying a plurality of flexible threads in each circumferential direction from each release wire at a plurality of positions along the release wires to reduce the diameter of the stent graft along the length of the stent graft.

19. A temporary diameter reduction constraint arrangement for a stent graft in combination with a stent graft, the stent graft comprising a biocompatible graft material tube having a tubular body of a selected diameter and a plurality of self expanding stents fastened thereto along the length of the tubular body, the plurality of self-expanding stents including a first end stent, a second end stent and an intermediate stent between the first and second end stents;

the stents comprising zig-zag stents comprising struts and bends therebetween, the constraint arrangement comprising two release wires extending longitudinally along the graft material tube, circumferentially spaced from and substantially parallel to each other, the release wires being stitched into the tubular body such that at least one stitch of each of the release wires is exposed to the outside of the tubular body in the region of the intermediate stent;

wherein the at least one exposed stitch of each of the release wires engages two threads, each of the two threads having one end engaged around the exposed stitch of its respective release wire and a second end engaged around a selected strut of the intermediate stent that is circumferentially spaced a selected distance away from its release wire in each circumferential direction from the respective release wires and drawn tight to compress the intermediate stent between the selected strut and the release wire and tied to reduce the circumference and hence the overall diameter of the stent graft.

* * * * *